United States Patent [19]
Bender et al.

[11] Patent Number: 6,093,825
[45] Date of Patent: Jul. 25, 2000

[54] METHODS FOR PREPARATION OF 1,2-DIHYDROQUINOLINES

[75] Inventors: Reinhold H. W. Bender, Valley Forge, Pa.; James P. Edwards, San Diego; Todd K. Jones, Solana Beach, both of Calif.

[73] Assignees: American Home Products, Madison, N.J.; Ligand Pharmaceuticals Incorporated, San Diego, Calif.

[21] Appl. No.: 09/086,004

[22] Filed: May 27, 1998

[51] Int. Cl.[7] .................... C07D 471/00; C07D 491/00; C07D 498/00; C07D 513/00
[52] U.S. Cl. .................. 546/62; 546/181; 556/410
[58] Field of Search ............... 556/410; 546/62, 546/181

[56] References Cited

U.S. PATENT DOCUMENTS

| | | | |
|---|---|---|---|
| 3,244,683 | 4/1966 | Kline | 546/181 |
| 3,466,270 | 9/1969 | Cook | 546/181 |
| 3,829,292 | 8/1974 | Monroy | 23/263 |
| 3,927,057 | 12/1975 | Takamizawa . | |
| 4,490,306 | 12/1984 | Acker | 564/79 |
| 4,514,570 | 4/1985 | Bowers . | |
| 4,526,970 | 7/1985 | Sheperd | 546/169 |
| 4,609,748 | 9/1986 | Sheperd | 556/410 |
| 4,617,395 | 10/1986 | Dockner et al. | 546/178 |
| 4,746,743 | 5/1988 | Yoshimura | 546/181 |
| 4,910,306 | 3/1990 | McKendry | 556/410 |
| 5,486,633 | 1/1996 | Pirrung et al. | 556/410 |
| 5,688,808 | 11/1997 | Jones et al. | 514/285 |
| 5,688,810 | 11/1997 | Jones et al. | 514/311 |
| 5,693,646 | 12/1997 | Jones et al. | 546/62 |
| 5,693,647 | 12/1997 | Jones et al. | 546/62 |
| 5,696,127 | 12/1997 | Jones et al. | 546/62 |
| 5,696,130 | 12/1997 | Jones et al. | 514/291 |
| 5,696,133 | 12/1997 | Jones et al. | 514/314 |

FOREIGN PATENT DOCUMENTS

WO 96/19458   6/1996   WIPO .

OTHER PUBLICATIONS

Manske et al., Organic Reactions, 7:59–98 (1953).
Vaughan, Org. Synth. Coll., vol. III, 329–32 (1955).
Edwards Chem. Abstr vol. 129 entry 161482, 1998.
Edwards J. Med. Chem vol. 41 pp. 303–310, 1998.

*Primary Examiner*—Mukund J. Shah
*Assistant Examiner*—Bruck Kifle
*Attorney, Agent, or Firm*—Lyon & Lyon LLP

[57] ABSTRACT

Methods for conversion of anilines to 1,2-dihydroquinolines. 1,2-dihydroquinoliiies are generated from combining an aniline, a silylating agent, and further condensing with a ketone in the presence of a catalyst. In one aspect, the silylation of the aniline may be performed in a one-step synthesis by adding the silylating, agent to the same reaction vessel as the ketone, aniline, and catalyst. In a second aspect, the 1,2-dihydroquinoline is generated in a two-step synthesis where an N-silyl aniline is formed prior to the addition of the ketone and catalyst.

15 Claims, No Drawings

6,093,825

METHODS FOR PREPARATION OF 1,2-DIHYDROQUINOLINES

FIELD OF THE INVENTION

This invention relates to methods for the synthesis of 1,2-dihydroquinoline compounds.

BACKGROUND OF THE INVENTION 1,2-dihydroquinolines are key intermediates in the preparation of a number of steroid receptor modulating compounds, and are prepared by a multi-step route culminating in the treatment of an aniline with acetone and iodine at elevated temperatures in a process known as the Skraup reaction, as shown below. See R. H. F. Manske et al., Organic Reactions 7: 59–98 (1953), and W. R Vaughan, Org. Synth. Coll. Vol III, 329–332 (1955).

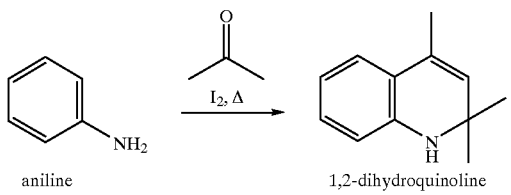

Many 1,2-dihydroquinolines are themselves steroid receptor modulating compounds. See, for example, PCT Int'l Publ. No. WO 96/19458; U.S. Pat. No. 5,693,647. Application of the traditional Skraup reaction to the synthesis of many of these 1,2-dihydroquinolines is problematic in that large quantities of a number of tarry by-products are formed that must be removed prior to use in further synthetic transformations, and the yields are generally low (15–50%). For example, as shown in U.S. Pat. No. 5,693,647, treatment of a polycyclic aniline, such as the amino-chloro-benzocoumarin shown below, with acetone and iodine at 130–135° C. affords only an 18% yield of the corresponding 1,2-dihydroquinoline. Furthermore, purification is very difficult due to the aforementioned by-product formation.

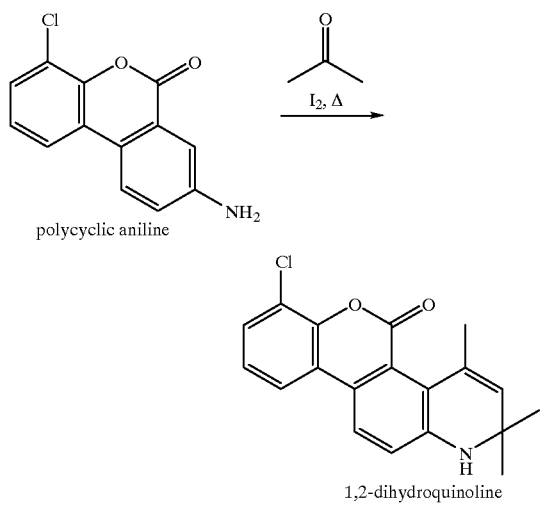

Several catalysts other than iodine have been reported to mediate the Skraup reaction such as iron trichloride, boron trifluoride, hydrofluoric acid, hydrochloric acid, p-toluenesulfonic acid, benzene sulfonic acid, and other acids, sometimes with less by-product formation. In addition, acidic ionic exchange resins have been used as catalysts, with improved yields of dihydroquinoline products. However, iodine has provided the most efficient synthesis of polycyclic 1,2-dihydroquinolines thus far. See, for example, U.S. Pat. Nos. 4,746,743, 4,514,570, and 3,829,292.

Therefore, a method for obtaining 1,2-dihydroquinolines in high yield with a significant reduction in the formation of by-products is needed, as compared to the traditional Skraup reaction.

The entire disclosures of the publications and references referred to above and hereafter in this specification are incorporated herein by reference.

SUMMARY OF THE INVENTION

The present invention is directed to novel methods for the conversion of anilines to 1,2-dihydroquinolines, such as. e.g., 1,2-dihydro-5-coumarino-[3,4-f]-quinolines, from aniline precursors in a novel modification of the Skraup synthesis. More particularly, the invention relates to synthetic methods wherein an aniline is combined with a silylating agent to form an N-silyl compound. The N-silyl compound is then condensed with a ketone in the presence of a catalyst to form the 1,2-dihydroquinoline. The new methods provide 1,2-dihydroquinolines in high yield with a significant reduction in the formation of by-products, as compared to the traditional Skraup reaction. The methods disclosed in this invention also provide for solvent conservation.

More particularly, the present invention is directed to improved methods of synthesis of steroid receptor modulating compounds such as 1,2-dihydroquinolines by converting a polycyclic aniline to a polycyclic N-silyl aniline and subsequent reaction with a ketone in the presence of a catalyst. The silylation of the aniline may be performed either in a one-step synthesis by adding the silylating agent to the same reaction vessel as the ketone, catalyst and aniline, or in a two-step synthesis wherein the N-silyl aniline is formed prior to addition of the ketone and catalyst. Either synthesis may be carried out with or without the presence of an inert co-solvent.

Other and further objects and advantages of the present invention will appear hereinafter.

DETAILED DESCRIPTION OF THE PREFERRED EMBODIMENTS

In accordance with the present invention, we have developed novel methods for preparing, 1,2-dihydroquinolines including polycyclic 1,2-dihydroquinolines such as, e.g., 1,2-dihydro-5-coumarino[3,4-f]quinolines from aniline precursurs such as, e.g., 3,4-benzocoumarin. These methods result in the production of 1,2-dihydroquinolines in high yield with reduced by-product formation.

In accordance with the present invention and as used herein, the following structures are provided for nomenclature purpose. In an effort to maintain consistency in the naming of compounds of similar structure but differing substituents, the compounds described herein are named according to the following general guidelines. Furthermore, the structures below are provided as a guide for the numbering system for the location of substituents and may be optionally substituted, including with aryl and heteroaryl rings. A 1,2-dihydroquinolinie is represented by the following structure:

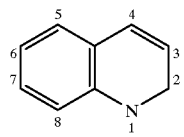

A 1,2-dihydro-5-coumarino[3,4-f]quinoline is represented by the following structure:

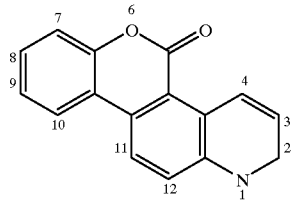

A 3,4-benzocoumarin is represented by following structure:

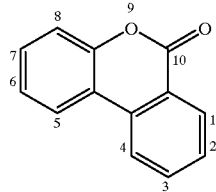

The 1,2-dihydroquinolines produced according to the present invention are useful as steroid receptor modulating compounds that have a variety of therapeutic applications, depending upon their specific biological activity, or as intermediates in the synthesis of steroid receptor modulating compounds. See for example, PCT Int'l Publ. No. WO 96/19458 corresponding to U.S. Pat. Nos. 5,688,808, 5,688,810, 5,693,646, 5,693,647, 5,696,127, 5,696,130, and 5,696,133. In particular, many 1,2-dihydro-5-coumarino-[3,4-f]-quinolines are known to be progesterone receptor (PR) modulators (e.g., PR agonists, partial agonists, and antagonists). See for example, PCT Int'l Publ. No. WO 96/19458 and U.S. Pat. No. 5,693,647.

Specifically, we have developed a novel method for preparing 1,2-dihydroquinolines which comprises treating an aniline with a silylating agent to form an N-silyl compound, which is subsequently treated with a ketone and at catalyst, with or without a co-solvent, at elevated temperatures, preferably 100–250° C. (Scheme I).

Scheme I.
Generation of 1,2-Dihydroquinoline from an N-Silyl Aniline

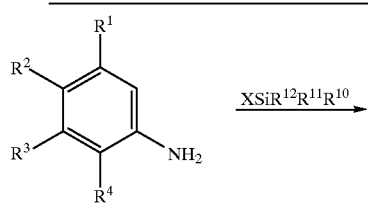

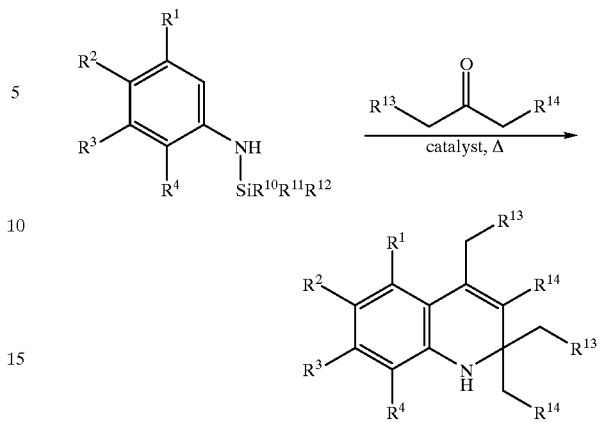

In a further embodiment of the invention, a modification of the above method has been developed. In this method, the aniline, silylating agent, and ketone may be combined in a single reaction vessel with a catalyst such as iodine, with or without a co-solvent such as dioxane, at elevated temperatures, preferably 100–250° C., to form the desired 1,2-dihydroquinoline product (Scheme II).

Scheme II:
A One-step Synthesis of 1,2-Dihydroquinoline from Aniline

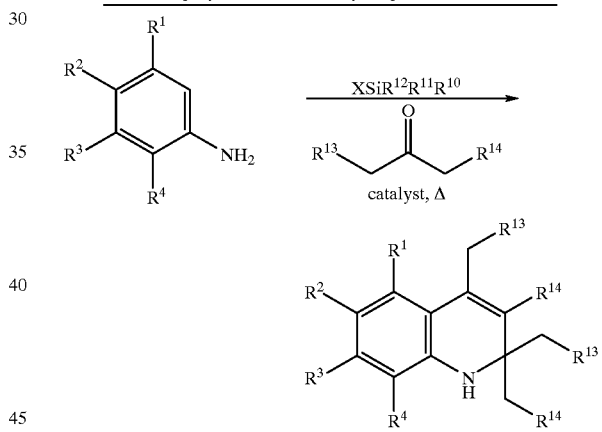

The anilines referenced above are recognized as aromatic amines, and may represent a polycyclic aromatic amine wherein $R^{1-4}$ may be optionally substituted. In addition, $R^1$ and $R^2$, $R^2$ and $R^3$, or $R^3$ and $R^4$ may combine to form an aryl or heteroaryl group, including mono- and polycyclic structures, optionally substituted at one or more positions. Exemplary anilines are shown below.

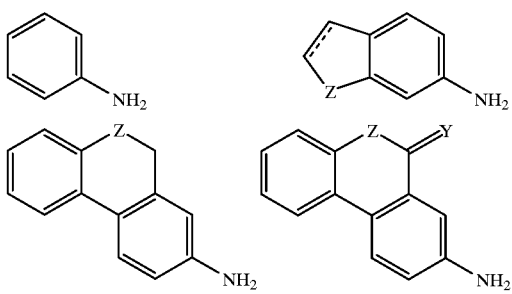

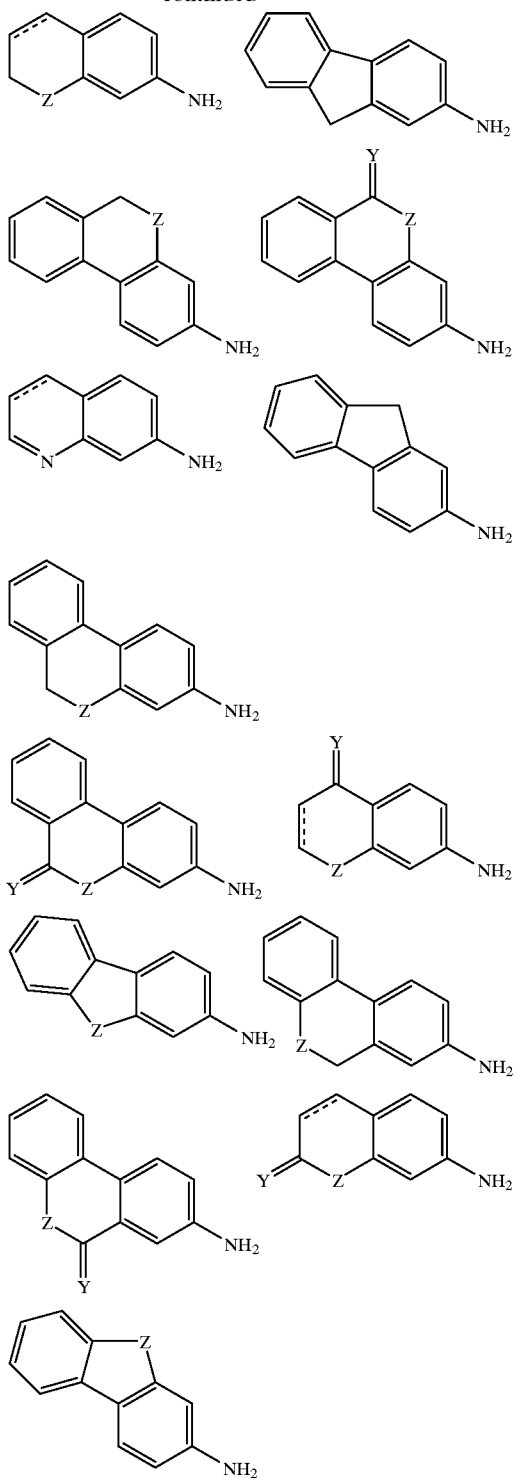

In the exemplary anilines shown above, Z represents one of O, S, NR, $CR_2$, or NCOR; Y represents one of O, S, or NR; and the dashed line represents an optional double bond. The above structures may be optionally substituted at one or more positions and are shown only as representative examples. The synthesis of these compounds is well known to those skilled in the art. Further, it is understood that these structures do not preclude other ring systems from the application of the methods of the current invention. See, for example, PCT Int'l Publ. No. WO 96/19458 corresponding to U.S. Pat. Nos. 5,688,808, 5,688,810, 5,693,646, 5,693,647, 5,696,127, 5,696,130, 5,696,133 and references therein.

The silylating agent, represented by $XSiR^{12}R^{11}R^{10}$ above, is recognized as any compound which can silylate an amine, such as a trialkysilyl halide, or preferably bis(trimethylsilyl) acetamide (BSA).

A preferred catalyst employed in the methods of this invention is iodine. Catalysts other than iodine may also be used in the methods of this invention such as, e.g., iron trichloride, boron trifluoride, hydrofluoric acid, hydrochloric acid, p-toluenesulfonic acid, and benzene sulfonic acid.

The ketone shown in the above reaction schemes is any ketone represented by the formula disclosed in the above schemes. Representative examples of ketones are, e.g., methyl ethyl ketone, and methyl isobutyl ketone. A preferred ketone is acetone.

The co-solvent employed in the methods of this invention is represented by any non-volatile non-reactive solvent such as, e.g., toluene, benzotrifluoride, or diglime. A preferred co-solvent is dioxane.

The 1,2-dihydroquinolines prepared by the methods of the present invention are understood to represent monocyclic and polycyclic structures as well as heterocyclic structures, and may be prepared from one of the representative corresponding aniline structures as shown above.

In the above process schemes, $R^{1-4}$ each independently represent H, $C_1$–$C_6$ alkyl, substituted $C_1$–$C_6$ alkyl, F, Cl, Br, I, CN, $CF_3$, $CF_2CF_3$, $CO_2R^7$, $CONR^7R^8$, $OR^9$, $NR^7R^9$, $SR^9$, $SOR^9$, or $SO_2R^9$; alternatively, $R^1$ and $R^2$, or $R^2$ and $R^3$ may combine to form one of:

wherein,

W represents one of O, NH, $NR^7$, $CH_2$, CHOH, C=O, OC=O, O=CO, $NR^7C$=O, NHC=O, O=$CNR^7$, O=CNH, SC=O, O=CS, O=$CCR^7R^8$, $CR^7R^8C$=O, $OCR^7R^8$, or $CR^7R^8O$;

Z represents one of O, $NR^7$, S, $CR^7R^8$, NH, $NCOR^7$;

Y represents O, S, or $NR^7$;

the dashed line represents an aromatic C—C bond;

$R^7$ represents H, $C_1$–$C_6$ alkyl, substituted $C_1$–$C_6$ alkyl or perfluoroalkyl, optionally substituted aryl or heteroaryl, or optionally substituted allyl;

$R^8$ represents H, $C_1$–$C_6$ alkyl, substituted $C_1$–$C_6$ alkyl or perfluoroalkyl, optionally substituted aryl or heteroaryl, or optionally substituted allyl;

alternatively, $R^7$ and $R^8$ may combine to form a four- to seven-membered ring;

$R^9$ represents $C_1$–$C_6$ alkyl, substituted $C_1$–$C_6$ alkyl or perfluoroalkyl, optionally substituted aryl or heteroaryl, or optionally substituted allyl;

$R^{10-12}$ independently represent $C_1$–$C_6$ alkyl, substituted $C_1$–$C_6$ alkyl, aryl or substituted aryl;

X represents chloro, bromo, or the following structure:

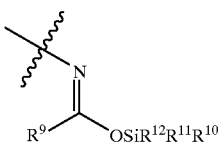

$R^{13-14}$ independently represent H, F, $OR^9$, $C_1-C_6$ alkyl, substituted $C_1-C_6$ alkyl, perfluoroalkyl, allyl, substituted allyl, aryl, substituted aryl, heteroaryl or substituted heteroaryl;

alternatively, $R^{13}$ and $R^{14}$ may combine to form an optionally substituted 5–7 membered ring;

$R^{15-18}$ independently represent H, $C_1-C_6$ alkyl, substituted $C_1-C_6$ alkyl, F, Cl, Br, I, CN, $CF_3$, $CF_2CF_3$, $CO_2R^7$, $CONR^7R^8$, $OR^9$, $NR^7R^9$, $SR^9$, $SOR^9$, or $SO_2R^9$;

$R^{19-20}$ independently represent H, Cl, Br, F, $C_1-C_4$ alkyl or perhaloalkyl, aryl, heteroaryl optionally substituted allyl, alkynyl, alkenyl, aryl, or heteroaryl;

the analogous positions on the structures within the schemes.

A preferred method, as shown below, begins with the formation of an aniline from a bromo anisole. Bromo anisoles can be obtained from commercial sources or, alternatively, can be obtained by routine chemical synthesis by those skilled in the art. The preparation of such anilines has previously been disclosed and can be obtained by routine chemical synthesis by those skilled in the art. See, for example, PCT Int. App. No. WO 96/19458 corresponding to U.S. Pat. Nos. 5,688,808, 5,688,810, 5,693,646, 5,693,647, 5,696,127, 5,696,130, and 5,696,133 the disclosures of which are herein incorporated by reference.

A preferred preparation of anilin, as shown below, begins with an orthobromoanisole, which is lithiated with, for example, n-butyllithium, and allowed to react with a trialkylborate such as trimethylborate. The intermediate acid is hydrolyzed with, for example, dilute hydrochloric acid, which produces the corresponding boronic acid. The boronic acid is coupled with a bromonitrobenzoate to give a biphenylcarboxylate. Intramolecular acylation and reduction of the nitro group produces the desired aniline compound.

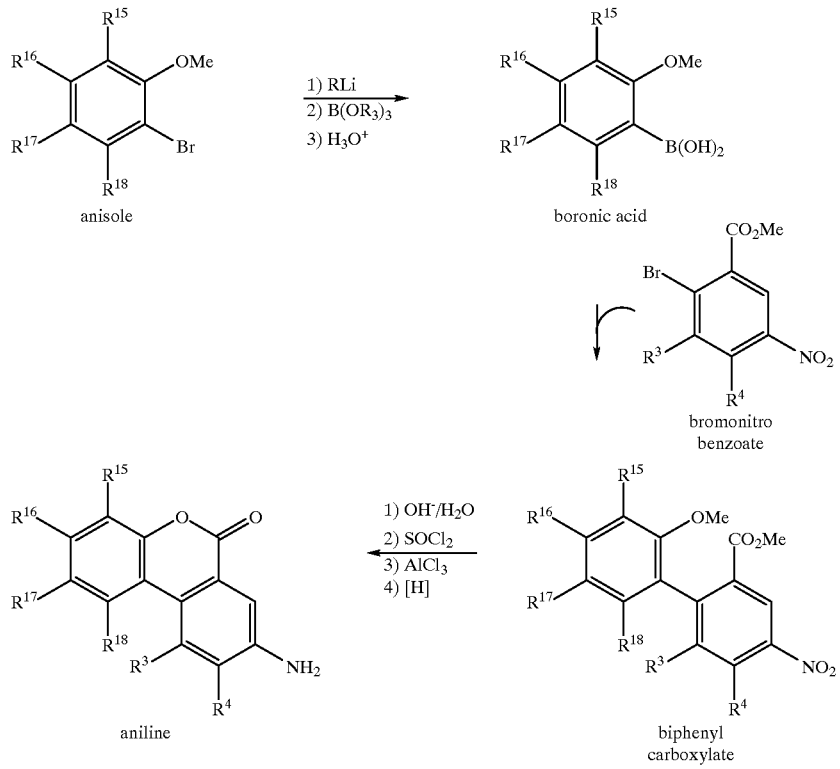

alternatively, $R^{19}$ and $R_{20}$ may combine to form an optionally substituted four- to seven-membered ring.

A sequence of steps is shown below for a preferred general process for formation of anilines and subsequent formation of dihydroquinolines. Further details for the preparation of anilines are shown in, e.g., U.S. Pat. No. 5,693,647. These steps may be used in the methods of this invention. However, it will be understood by those skilled in the art that other functionalities disclosed herein at the indicated positions of the various anilines and dihydroquinoline compounds may also comprise potential substituents for The anilines as prepared above may be employed in the methods of this invention shown in Scheme I or Scheme II in the preparation of 1,2-dihydroquinolines from aniline. According to the method of Scheme I, an aniline, such as the polycyclic aniline shown above, is treated with a silylating agent, such as trialkylsilyl chloride or N,O-bis(trialkylsilyl) amide, to form an N-silyl aniline as shown below. The N-silyl compound is subsequently treated with a ketone such as acetone, and a catalyst such as iodine, with or without a co-solvent such as 1,4-dioxane, at elevated temperatures, preferably 100–250° C., to yield the desired 1,2- dihydroquinoline. A more detailed example of the method of Scheme I is provided below in Example 1.

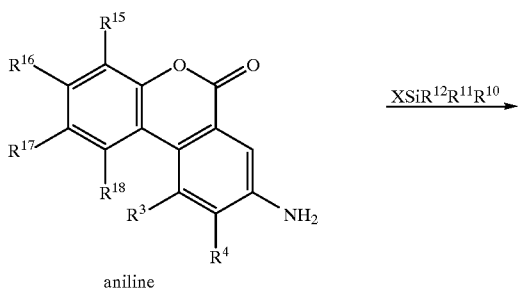
aniline

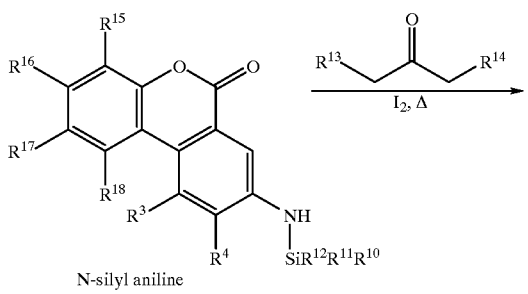
N-silyl aniline

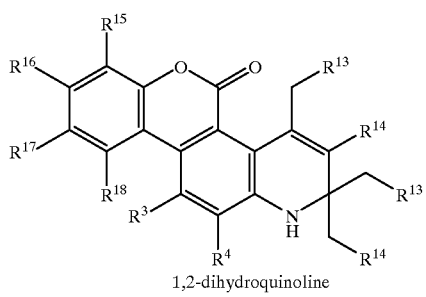
1,2-dihydroquinoline

Alternatively, using the method as shown in Scheme II, an aniline a silylating agent, and a ketone may be combined in a single reaction vessel with a catalyst such as iodine, with or without a co-solvent such as dioxane, at elevated temperatures, preferably 100–250° C., to yield the desired 1,2-dihydroquinoline compound as shown below. Examples 2, 3, and 4 below show the method of preparing 1,2-dihydroquinolines according to Scheme II.

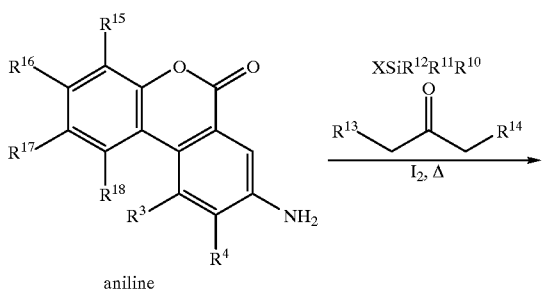
aniline

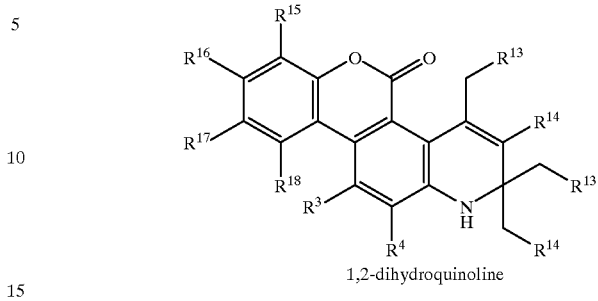
1,2-dihydroquinoline

In the sequence shown above, $R^{3-18}$ have the definitions described previously.

The methods of the current invention are shown by the following illustrative examples.

EXAMPLES

Example 1

Step A

6-Fluoro-2-(trimethylsilylamino)-3,4-benzocoumarin (N-silyl aniline where $R^{3-4}=R^{13-14}=R^{15-16}=R^{18}=H$; $R^{17}=$ fluoro; $R^{10-12}=$methyl). In a 100-mL r.b. flask, a suspension of 2-amilno-6-fluoro-3,4-benzoeoumarin (0.50 g, 2.2 mmol) in acetonitrile (50 mL) was treated with N,O-bis (trimethylsilyl)acetamide (2.0 mL, 8.1 mnmol, 3.7 equiv) and chliorotrimetlhylsilane (20 μL). The reaction mixture was stirred for 4 h and the volatiles were removed in vacuo to afford the N-trimethylsilyl aniline as a yellow powder. Data for 6-fluoro-2-(trimethylsilylamiho)-3,4-benzocoumarin: $^1$H NMR (400 MHz, CDCl$_3$): 7.80 (d, J=8.7 Hz, 1H), 7.59 (d, J=2.6 Hz, 1H); 7.56 (dd, J=9.3, 2.9 Hz, 1H); 7.28 (dd, J=9.0, 4.7 Hz, 1H); 7.12 (dd, J=8.7, 2.7 Hz, 1H); 7.05 (m, 1H); 3.88 (s, 1H); 0.35 (s, 9H).

Step B

9-Fluoro-1,2-dihydro-2,2,4-trimethyl-5-isocoumarino[3,4-f]quinoline (1,2-dihydroquinoline, where $R^{3-4}=R^{13-14}=R^{15-16}=R^{18}=H$; $R^{17}=$fluoro). In a 200-mL resealable pressure tube, a solution of 6-fluoro-2-(trimethylsilylamino)-3,4-benzocoumariin as prepared above was dissolved in acetone (100 mL) and treated with iodine (0.25 g). The pressure tube was sealed and heated to 125° C. for 40 h. The reaction mixture was cooled to room temperature, concentrated to remove the bulk of the acetone, and dissolved in EtOAc (40 mL). The organic layer was washed with 1.0 N Na$_2$S$_2$O$_3$ (2×40 mL) and brine (1×40 mL). The aqueous layers were extracted with EtOAc (2×40 mL). The combined organic layers were dried (MgSO$_4$), filtcred, and concentrated to afford an orange solid. Purification by silica gel chromatography (CH$_2$Cl$_2$/hexanes, 1:1 to 1.5:1 gradient) afforded 0.59 g (88%) of product as a bright yellow solid. $^1$H NMR (acetone-d$_6$): 7.95 (d, J=8.7 Hz, 1H); 7.83 (dd, J=10.1, 2.9 Hz, 1H); 7.29 (dd, J=9.0, 4.9 Hz, 1H); 7.22 (d, J=8.7 Hz, 1H); 7.17 (m, 1H); 6.25 (br s, 1H); 5.54 (t, J=1.2 Hz, 1H); 2.06 (s, 3H); 1.30 (s, 6H): $^{13}$C{$^1$H} NMR (acetone-d$_6$): 160.2 (d, J$_{C-F}$=239 Hz); 159.9. 148.2, 147.3, 132.9, 131.7, 125.3, 123.0, 121.9, 121.8, 119.1, 118.9 (d, $J_{C-F}$=9.0 Hz); 115.6 (d, $J_{C-F}$=25 Hz); 108.9 (d, $J_{C-F}$=26 Hz); 51.0, 28.5, 21.6.

Example 2

9-Fluoro-1,2-dihydro-2,2,4-trimethyl-5-isocoumarino[3,4-f]quinoline (1,2-dihydroquinioline, where $R^{3-4}=R^{13-14}=R^{15-16}=R^{18}$=H; $R^{17}$=fluoro). In a 600-mL resealable pressure tube, a solution of 2-amino-6-fluoro-3,4-benzocoumarin (4.27 g) was dissolved in acetone (300 mL) and dioxane (100 mL) and treated with iodine (1.9 g) and N,O-bis(trimethylsilyl)acetamide (13.8 mL). The pressure tube was sealed and heated to 125–130° C. for 48 h. The reaction mixture was cooled to room temperature, concentrated to remove the bulk of the acetone, and dissolved in EtOAc (200 mL). The organic layer was washed with 1.0 N $Na_2S_2O_3$ (2×200 mL) and brine (1×200 mL). The aqueous layers were extracted with EtOAc (2×200 mL). The combined organic layers were dried ($MgSO_4$), filtered, and concentrated to afford an orange solid. Purification by silica gel chromatography ($CH_2Cl_2$/hexanes, 1:1 to 1.5:1 gradient) afforded 3.0 g (52%) of product as a bright yellow solid, identical to the material prepared above (Example 1).

Example 3

7-Chloro-1,2-dihydro-2,2,4-trimethyl-5-coumarino[3,4-f]quinoline (1,2-dihydroquinoline, where $R^{15}$=chloro; $R^{3-4}=R^{13-14}=R^{16-18}$=H). In a 600-mL resealable pressure tube, a susprnsion of 2-amino-8-chloro-3,4-benzocoumarin (1.24 g) in acetone (200 ml,) was treated with iodine (0.50 g) and N,O-bis(trimethylsilyl)acetamide (0.5 mL). The tube was sealed and heated to 125–135° C. for 72 h. The tube was allowed to cool to room temperature and the bulk of the acetone was removed in vacuo. The residue was dissolved in EtOAc (120 mL). The organic layer was washed with 0.5 N $Na_2S_2O_3$ (2×100 mL), $H_2O$ (1×100 mL), and brine (1×100 mL). The aqueous layers were extracted with EtOAc (2×100 mL). The combined organic layers were dried ($MgSO_4$), filtered, and concentrated to afford an orange solid. Purification by silica gel chromatography (hexane/EtOAc, 4:1 to 2:1 gradient) afforded 923 mg (56%) of product as a yellow solid. $^1$H NMR (400 MHz. acetone-$d_6$): 8.04 (dd, J=8.1, 1.1 Hz, 1H); 7.98 (d, J=8.7 Hz, 1H); 7.48 (dd, J=9.0, 1.1 Hz, 1H); 7.28 (t, J=8.8 Hz, 1H); 7.23 (d, J=8.6 Hz, 1H), 6.24 (br s, 1H); 5.55 (d, J=1.2 Hz, 1H); 2.08 (s, 3H); 1.31 (s, 6H).

Example 4

1,2-Dihydro-9-methoxy-2,2,4-trimethyl-5-coumarino[3,4-f]quinoline (1,2-dihydroquinoline, where $R^{5-6}=R^{13-14}=R^{15-16}=R^{18}$=H; $R^{17}$=methoxy). In a 600-mL resealable pressure tube, a suspension of 2-amino-6-methoxy-3,4-benzocoumarin (1.50 g) in acetone (300 mL) was treated with iodine (0.60 g) and N,O-bis(trimetfylsilyl)acetamide (6.2 mL). The tube was sealed and heated to 125–135° C. for 48 h. The tube was allowed to cool to room temperature and the bulk of the acetone was removed in vacuo. The residue was dissolved in EtOAc (200 mL). The organic layer was washed with 0.5 N $Na_2S_2O_3$ (2×200 mL), $H_2O$ (1×200 mL), and brine (1×200 mL). The aqueous layers were extracted with EtOAc (2×200 mL). The combined organic layers were dried ($MgSO_4$), filtered, and concentrated to afford an orange solid. Purification by silica gel chromatography (3% EtOAc in hexane/$CH_2Cl_2$, 3:1 to 2:1 gradient) afforded 910 mg (45%) of product as a yellow solid. $^1$H NMR (400 MHz, acetone-$d_6$): 7.73 (d, J=8.6 Hz, 1H); 7.35 (d, J=2.8 Hz, 1H); 7.23 (d, J=8.9 Hz, 1H); 7.00 (d, J=8.6 Hz, 1H); 6.92 (dd, J=8.9, 2.8, Hz 1H); 5.57 (s, 1H); 4.29 (br s, 1H); 3.88 (s, 3H); 2.11 (d, J=1.1 Hz, 3H); (s, 6H).

As shown in the above examples, relatively high yields of the desired 1,2-dihydroquinoline products are obtained utilizing the disclosed methods. The desired products are also readily purified due to decreased by-product formation. In addition, the disclosed methods also provide for solvent conservation. For example, the traditional Skraup reaction, run at the reagent concentration used in the disclosed methods, provides approximately 18–35% yields. A fourfold dilution of reagents in the traditional Skraup route is required to achieve yields comparable to those obtained with the new method and, further, there is no reduction in by-product formation.

While embodiments and applications of this invention have been shown and described, it would be apparent to those skilled in the art that many more modifications and further embodiments of this invention are possible without departing from the inventive concepts herein. The invention, therefore, is not to be restricted except in the spirit of the appended claims.

We claim:

1. A method for the preparation of 1,2-dihydroquinolines of the formula:

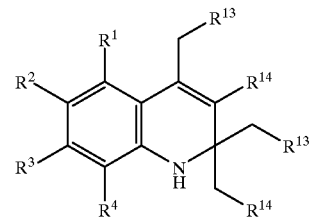

wherein, $R^{1-4}$ each independently represent H, $C_1$–$C_6$ alkyl optionally substituted with $C_1$–$C_6$ alkyl or halogen; F, Cl, Br, I, CN, CF3, $CF_2CF_3$, $CO_2R^7$, $CONR^7R^8$, $OR^9$, $NR^7R^9$, $SR^9$, $SOR^9$, or $SO_2R^9$, or, alternatively, $R^1$ and $R^2$, or $R^2$ and $R^3$ may combine to form one of:

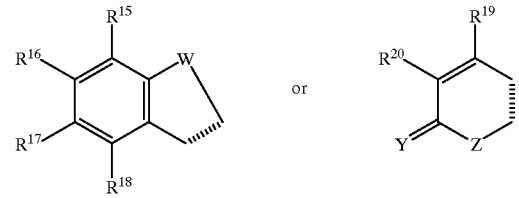

wherein,

W represents one of O, NH, $NR^7$, $CH_2$, CHOH, C=O, OC=O, O=CO, $NR^7C$=O, NHC=O, O=$CNR^7$, O=CNH, SC=O, O=CS, O=$CCR^7R^8$, $CR^7R^8C$=O, $OCR^7R^8$, or $CR^7R^8O$;

Z represents one of O, $NR^7$, S, $CR^7R^8$, NH, $NCOR^7$;

Y represents O, S, or $NR^7$;

the dashed line represents an aromatic C—C bond;

$R^7$ represents H, $C_1$–$C_6$ alkyl optionally substituted with $C_1$–$C_6$ alkyl or halogen, or $C_1$–$C_6$ perfluoroalkyl, phenyl, heteroaryl, or allyl and wherein the phenyl, heteroaryl or allyl groups can be optionally substituted with $C_1$–$C_6$ alkyl or halogen;

$R^8$ represents H, $C_1$–$C_6$ alkyl optionally substituted with $C_1$–$C_6$ alkyl or halogen, or $C_1$–$C_6$ perfluoroalkyl, phenyl, heteroaryl, or allyl and wherein the phenyl, heteroaryl or allyl groups can be optionally substituted with $C_1$–$C_6$ alkyl or halogen;

or, alternatively, $R^7$ and $R^8$ may combine to form a four- to seven-membered cycloalkyl or cycloalkene ring;

$R^9$ represents H, $C_1$–$C_6$ alkyl optionally substituted with $C_1$–$C_6$ alkyl or halogen, or $C_1$–$C_6$ perfluoroalkyl, phenyl, heteroaryl, or allyl and wherein the phenyl, heteroaryl or allyl groups can be optionally substituted with $C_1$–$C_6$ alkyl or halogen;

$R^{15-18}$ independently represent H, $C_1$–$C_6$ alkyl optionally substituted with $C_1$–$C_6$ alkyl or halogen, F, Cl, Br, I, CN, CF3, $CF_2CF_3$, $CO_2R^7$, $CONR^7R^8$, $OR^9$, $NR^7R^9$, $SR^9$, $SOR^9$, or $SO_2R^9$;

$R^{19-20}$ independently represent H, Cl, Br, F, $C_1$–$C_4$ alkyl or $C_1$–$C_6$ perhaloalkyl, phenyl, heteroaryl, allyl, alkynyl, or alkenyl, and wherein the allyl, alkynyl alkenyl phenyl, heteroaryl or alkyl groups can be optionally substituted with $C_1$–$C_6$ alkyl or halogen:

or, alternatively, $R^{19}$ and $R^{20}$ may combine to form a four to seven-membered cycloalkyl or cycloalkene ring, optionally substituted with $C_1$–$C_6$ alkyl or halogen, which comprises the steps of:

a) treating an aniline compound of structural formula:

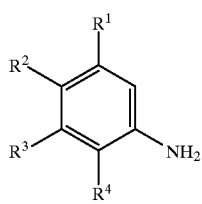

with a silylating agent of structural formula:

$XSiR^{12}R^{11}R^{10}$ where X represents chloro, bromo, or the following structure:

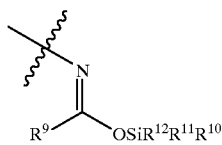

to form an N-silyl aniline of structural formula:

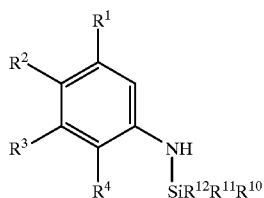

where $R^{10-12}$ independently represent $C_1$–$C_6$ alkyl or phenyl wherein the alkyl and phenyl can be optionally substituted with $C_1$–$C_6$ alkyl or halogen, and b) treating the N-silyl aniline with a ketone of structural formula:

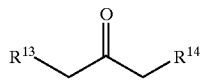

and a catalyst, with or without a co-solvent, at elevated temperatures to produce a 1,2-dihydroquinoline, where $R^{13-14}$ independently represent H, F, $OR^9$, $C_1$–$C_6$ alkyl optionally substituted with $C_1$–$C_6$ alkyl or halogen, $C_1$–$C_6$ perfluoroalkyl, phenyl, heteroaryl, or allyl and wherein the phenyl, heteroaryl or allyl groups can be optionally substituted with $C_1$–$C_6$ alkyl or halogen or, alternatively, $R^{13}$ and $R^{14}$ may combine to form a 5–7 membered cycloalkyl or cycloalkene ring optionally substituted with $C_1$–$C_6$ alkyl or halogen.

2. The method of claim 1 wherein said silylating agent of step (a) is a trialkylsilyl chloride or N,O-bis(trialkylsilyl) amide.

3. The method of claim 1 wherein said ketone of step (b) is acetone.

4. The method of claim 1 wherein said catalyst of step (b) is iodine.

5. The method of claim 1 wherein said co-solvent of step (b) is 1,4-dioxane.

6. The method of claim 1 wherein said elevated temperature is 100–250° C.

7. The method of claim 1 wherein said 1,2-dihydroquinioline product produced has the structural formula:

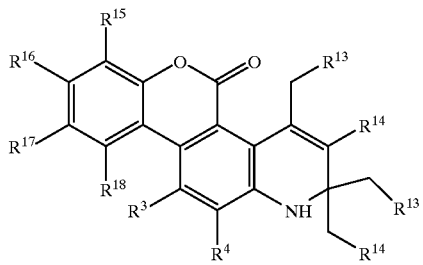

or, alternatively, $R^7$ and $R^8$ may combine to form a four- to seven-membered ring;

$R^9$ represents $C_1$–$C_6$ alkyl, substituted $C_1$–$C_6$ alkyl or perfluoroalkyl, optionally substituted aryl or heteroaryl, or optionally substituted allyl;

$R^{15-18}$ independently represent H, $C_1$–$C_6$ alkyl, substituted $C_1$–$C_6$ alkyl, F, Cl, Br, I, CN, $CF_3$, $CF_2CF_3$, $CO_2R^7$, $CONR^7R^8$, $OR^9$, $NR^7R^9$, $SR^9$, $SOR^9$, or $SO_2R^9$;

$R^{19-20}$ independently represent H, Cl, Br, F, $C_1$–$C_4$ alkyl or perhaloalkyl, aryl, heteroaryl optionally substituted allyl, alkynyl, alkenyl, aryl, or heteroaryl, or, alternatively, $R^{19}$ and $R^{20}$ may combine to form an optionally substituted four to seven-membered ring, which comprises treating an aniline of structural formula:

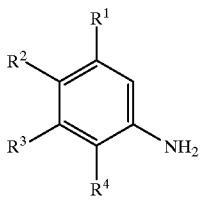

with a silylating agent of structural formula:

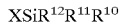

where X represents chloro, bromo, or the following structure:

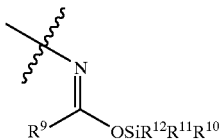

and a ketone of structural formula:

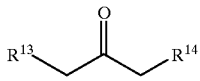

and a catalyst, with or without a co-solvent, in a single reaction vessel at elevated temperatures to produce a 1,2-dihydroquinoline, where $R^{13-14}$ independently represent H, F, $OR^9$, $C_1$–$C_6$ alkyl, substituted $C_1$–$C_6$ alkyl, perfluoroalkyl, allyl, substituted allyl, aryl, substituted aryl, heteroaryl or substituted heteroaryl or, alternatively, $R^{13}$ and $R^{14}$ may combine to form an optionally substituted 5–7 membered rings.

8. A method for the preparation of 1,2-dihydroquinolines of the following formula:

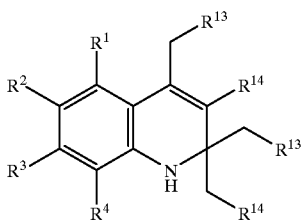

wherein, $R^{1-4}$ each independently represent H, $C_1$–$C_6$ alkyl optionally substituted with $C_1$–$C_6$ alkyl or halogen, F, Cl, Br, I, CN, $CF_3$, $CF_2CF_3$, $CO_2R^7$, $CONR^7R^8$, $OR^9$, $NR^7R^9$, $SR^9$, $SOR^9$, or $SO_2R^9$, or, alternatively, $R^1$ and $R^2$, or $R^2$ and $R^3$ may combine to form one of:

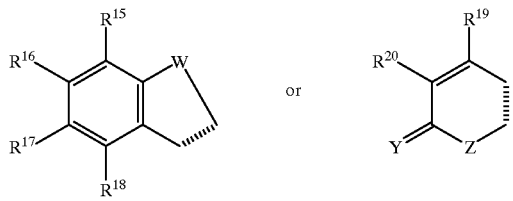

wherein,
W represents one of O, NH, $NR^7$, $CH_2$, CHOH, C=O, OC=O, O=CO, $NR^7$C=O, NHC=O, O=$CNR^7$, O=CNH, SC=O, O=CS, O=$CCR^7R^8$, $CR^7R^8$C=O, $OCR^7R^8$, or $CR^7R^8$O;

Z represents one of O, $NR^7$, S, $CR^7R^8$, NH, $NCOR^7$;

Y represents O, S, or $NR^7$;

the dashed line represents an aromatic C—C bond;

$R^7$ represents H, $C_1$–$C_6$ alkyl opltionally substituted with $C_1$–$C_6$ alkyl or halogen, or $C_1$–$C_6$ perfluoroalkyl, phenyl, heteroaryl, or allyl and wherein the phenyl heteroaryl or allyl groups can be optionally substituted with $C_1$–$C_6$ alkyl or halogen;

$R^8$ represents H, $C_1$–$C_6$ alkyl optionally substituted with $C_1$–$C_6$ alkyl or halogen, or $C_1$–$C_6$ perfluoroalkyl, phenyl, heteroaryl, or allyl and wherein the phenyl, heteroaryl or allyl groups can be optionally substituted with $C_1$–$C_6$ alkyl or halogen, or, alternatively, $R^7$ and $R^8$ may combine to form a four- to seven-membered cycloalkyl ring;

$R^9$ represents H, $C_1$–$C_6$ alkyl optionally substituted with $C_1$–$C_6$ alkyl or halogen, or $C_1$–$C_6$ perfluoroalkyl, phenyl, heteroaryl, or allyl and wherein the phenyl, heteroaryl or allyl groups can be optionally substituted with $C_1$–$C_6$ alkyl or halogen;

$R^{15-18}$ independently represent H, $C_1C_6$ alkyl, F, Cl, Br, I, CN, $CF_3$, $CF_2CF_3$, $CO_2R^7$, $CONR^7R^8$, $OR^9$, $NR^7R^9$, $SR^9$, $SOR^9$, or $SO_2R^9$;

$R^{19-20}$ independently represent H, Cl, Br, F, $C_1$–$C_4$ alkyl or $C_1$–$C_6$ perhaloalkyl, phenyl, heteroaryl, allyl, alkynyl, or alkenyl, and wherein the allyl, alkynyl alkenyl phenyl, heteroaryl or alkyl groups can be optionally substituted with $C_1$–$C_6$ alkyl or halogen, or, alternatively, $R^{19}$ and $R^{20}$ may combine to form a four to seven-membered cycloalkyl or cycloalkene ring, optionally substituted with $C_1$–$C_6$ alkyl or halogen, which comprises treating an aniline of structural formula:

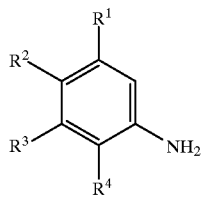

with a silylating agent of structural formula:

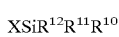

where X represents chloro, bromo, or the following structure:

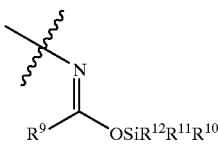

and a ketone of structural formula:

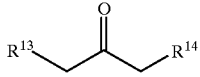

and a catalyst, with or without a co-solvent, in a single reaction vessel at elevated temperatures to produce a 1,2-dihydroquinoline,
where $R^{10-12}$ independently represent $C_1$–$C_6$ alkyl or phenyl wherein the alkyl and phenyl can be optionally substituted with $C_1$–$C_6$ alcyl or halogen, and
where $R^{13-14}$ independently represent H, F, $OR^9$, $C_1$–$C_6$ alkyl optionally substituted with $C_1$–$C_6$ alkyl or halogen, $C_1$–$C_6$ perfluoroalkyl, phenyl, heteroaryl, or allyl and wherein the aryl, heteroaryl or allyl groups can be optionally substituted with $C_1$–$C_6$ alkyl or halogen or,
alternatively, $R^{13}$ and $R^{14}$ may combine to form a 5–7 membered cycloalkyl or cycloalkene ring optionally substituted with $C_1$–$C_6$ alkyl or halogen.

9. The method of claim 8 wherein said silylating agent is a trialkylsilyl chloride or N,O-bis(trialkylsilyl)amide.

10. The method of claim 8 wherein said ketone is acetone.

11. The method of claim 8 wherein said catalyst is iodine.

12. The method of claim 8 wherein said co-solvent is 1,4-dioxane.

13. The method of claim 8 wherein said elevated temperature is 100–250° C.

14. The method of claim 8 wherein said 1,2-dihydroquinoline produced has the structural formula:

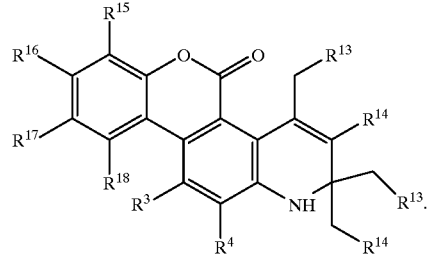

15. A method for the preparation of 1,2-dihydroquinolines which comprises:

treating an optionally substituted monocyclic or polycyclic aryl or hetemoaryl aniline with a silylating agent, a ketone, and a catalyst with or without a co-solvent, in a single reaction vessel at elevated temperatures.

* * * * *